United States Patent
Tabak et al.

(10) Patent No.: US 11,055,789 B1
(45) Date of Patent: *Jul. 6, 2021

(54) SYSTEMS AND METHODS FOR INSURANCE FRAUD DETECTION

(71) Applicant: Pearl Inc., West Hollywood, CA (US)

(72) Inventors: Joshua Alexander Tabak, Los Angeles, CA (US); Adam Michael Wilbert, Los Angeles, CA (US); Mustafa Alammar, Los Angeles, CA (US); Rohit Sanjay Annigeri, Los Angeles, CA (US); Cambron Neil Carter, Los Angeles, CA (US)

(73) Assignee: Pearl Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,418

(22) Filed: Sep. 4, 2020

Related U.S. Application Data (60) Provisional application No. 62/962,828, filed on Jan. 17, 2020.

(51) Int. Cl.
*G06Q 40/08* (2012.01)
*G16H 15/00* (2018.01)
(Continued)

(52) U.S. Cl.
CPC .......... *G06Q 40/08* (2013.01); *G06K 9/6215* (2013.01); *G16H 15/00* (2018.01); *G16H 30/20* (2018.01); *H04L 9/3247* (2013.01); *H04L 67/40* (2013.01)

(58) Field of Classification Search
CPC .............................................. G06Q 50/22–24
(Continued)

(56) References Cited

U.S. PATENT DOCUMENTS

| 5,839,438 A | 11/1998 | Grattinger et al. |
| 6,409,504 B1 | 6/2002 | Jones et al. |

(Continued)

FOREIGN PATENT DOCUMENTS

| CA | 2275574 C | 7/2003 |
| CN | 107 871 285 | 4/2018 |

(Continued)

OTHER PUBLICATIONS

S.B. Kotsiantis, "Supervised Machine Learning: A Review of Classification Techniques", Jul. 16, 2007, Informatica 31 (2007) 249-268, all pages. (Year: 2007).*

(Continued)

*Primary Examiner* — Jason S Tiedeman
*Assistant Examiner* — Jessica Marie Webb
(74) *Attorney, Agent, or Firm* — Knobbe, Martens, Olson & Bear, LLP (57) ABSTRACT

Systems and methods are described for automatically identifying fraud, waste or abuse in health insurance claims submitted to insurance companies by healthcare providers. Insurance claim information and at one image associated with the insurance claim may be received, where the image has been submitted by a healthcare provider to an insurance carrier as supporting evidence of a medical service performed by the healthcare provider. The system may generate a digital signature representing the image, then may compare the digital signature generated for the image to previously generated digital signatures of other images that have been submitted in association with other insurance claims. The system may then determine a likelihood that the given insurance claim is associated with fraud, waste or abuse, based in part on whether the digital signature is identical or close to one or more of the previously generated digital signatures.

19 Claims, 8 Drawing Sheets

(51) Int. Cl.
  *G16H 30/20* (2018.01)
  *H04N 21/643* (2011.01)
  *H04L 9/32* (2006.01)
  *G06N 20/00* (2019.01)
  *H04L 29/06* (2006.01)
  *G06K 9/62* (2006.01)

(58) Field of Classification Search
  USPC .................................................... 705/4, 2
  See application file for complete search history.

(56) References Cited

U.S. PATENT DOCUMENTS

| | | |
|---|---|---|
| 6,736,776 B2 | 5/2004 | Miles |
| 7,269,278 B2 | 9/2007 | Cong et al. |
| 7,421,398 B2 | 9/2008 | Kimmel |
| 7,472,275 B2 | 12/2008 | Arnouse |
| 7,602,965 B2 | 10/2009 | Hong et al. |
| 7,822,621 B1 | 10/2010 | Chappel |
| 8,417,010 B1 | 4/2013 | Colby |
| 8,463,716 B2 | 6/2013 | Montgomery et al. |
| 8,687,859 B2 | 4/2014 | Yan et al. |
| 8,761,493 B2 | 6/2014 | Chen et al. |
| 8,768,016 B2 | 7/2014 | Pan et al. |
| 8,929,635 B2 | 1/2015 | Chen et al. |
| 9,020,236 B2 | 4/2015 | Wang et al. |
| 9,339,245 B2 | 5/2016 | Colby |
| 9,477,649 B1 | 10/2016 | Davidson et al. |
| 9,839,402 B2 | 12/2017 | Colby |
| 9,886,178 B2 | 2/2018 | Kendall et al. |
| 10,043,073 B2 | 8/2018 | Ross et al. |
| 10,049,457 B2 | 9/2018 | Abraham et al. |
| 10,201,318 B2 | 2/2019 | Tsuji et al. |
| 10,410,363 B2 | 9/2019 | Dekel et al. |
| 10,426,351 B2 | 10/2019 | Abrams et al. |
| 10,722,191 B2 | 7/2020 | Colby |
| 10,818,386 B2* | 10/2020 | Yao .................... G06N 5/04 |
| 10,869,608 B2* | 12/2020 | Dormer ................ A61B 5/725 |
| 10,902,940 B2* | 1/2021 | Lyman .................. G06T 5/002 |
| 10,937,108 B1 | 3/2021 | Tabak et al. |
| 2005/0203777 A1* | 9/2005 | Rosenfeld .............. G06Q 30/04 705/3 |
| 2006/0147872 A1 | 7/2006 | Andreiko |
| 2006/0173985 A1* | 8/2006 | Moore ................ G06F 21/6254 709/223 |
| 2007/0217648 A1 | 9/2007 | Muehlbauer |
| 2007/0271226 A1 | 11/2007 | Zhang et al. |
| 2007/0294104 A1 | 12/2007 | Boaz et al. |
| 2009/0076960 A2* | 3/2009 | Hamel .................. G06Q 10/10 705/50 |
| 2011/0119088 A1* | 5/2011 | Gunn .................... G16H 10/60 705/3 |
| 2011/0153351 A1* | 6/2011 | Vesper .................. G16H 30/20 705/2 |
| 2011/0176712 A1 | 7/2011 | Hill et al. |
| 2012/0076422 A1 | 3/2012 | Yang et al. |
| 2012/0148986 A1 | 6/2012 | Yan et al. |
| 2012/0230560 A1 | 9/2012 | Spitz et al. |
| 2013/0022251 A1 | 1/2013 | Chen et al. |
| 2013/0185331 A1 | 7/2013 | Conemac |
| 2014/0142984 A1* | 5/2014 | Wright .................. G06F 16/951 705/3 |
| 2014/0149128 A1 | 5/2014 | Getchius |
| 2014/0278529 A1* | 9/2014 | Matos .................... G16H 80/00 705/3 |
| 2014/0314288 A1 | 10/2014 | Roychowdhury et al. |
| 2014/0355880 A1 | 12/2014 | Xuan et al. |
| 2014/0379361 A1* | 12/2014 | Mahadkar .............. G06Q 10/10 705/2 |
| 2015/0046181 A1 | 2/2015 | Adjaoute |
| 2015/0237106 A1* | 8/2015 | Golay ................. H04N 5/23206 709/203 |
| 2016/0014288 A1 | 1/2016 | Ono |
| 2016/0038092 A1 | 2/2016 | Golay |
| 2016/0196389 A1* | 7/2016 | Moturu .................. G16H 50/20 705/2 |
| 2017/0053562 A1* | 2/2017 | Bova ...................... G09B 23/28 |
| 2017/0083672 A1* | 3/2017 | Juneau .................. G16H 40/20 |
| 2017/0161439 A1* | 6/2017 | Raduchel ............. G06Q 10/063 |
| 2018/0122509 A1* | 5/2018 | Christiansson ........ G16H 10/60 |
| 2018/0174367 A1 | 6/2018 | Marom |
| 2018/0206940 A1 | 7/2018 | Kopelan et al. |
| 2018/0235437 A1 | 8/2018 | Ozerov et al. |
| 2018/0325484 A1 | 11/2018 | Patel |
| 2018/0366225 A1 | 12/2018 | Mansi et al. |
| 2019/0066835 A1 | 2/2019 | Lyman et al. |
| 2019/0110753 A1 | 4/2019 | Zhang et al. |
| 2019/0130566 A1 | 5/2019 | Niemeijmer et al. |
| 2019/0236614 A1 | 8/2019 | Burgin et al. |
| 2019/0313963 A1 | 10/2019 | Hillen |
| 2020/0012884 A1 | 1/2020 | Zhao et al. |
| 2020/0134823 A1* | 4/2020 | Emoto .................... G06T 5/002 |
| 2020/0138518 A1 | 5/2020 | Lang |
| 2020/0146646 A1 | 5/2020 | Tuzoff |
| 2020/0305808 A1 | 10/2020 | Ezhov et al. |
| 2020/0381105 A1 | 12/2020 | Bernard et al. |
| 2021/0012426 A1* | 1/2021 | Brooks .................. G06Q 10/10 |
| 2021/0073977 A1 | 3/2021 | Carter et al. |
| 2021/0074425 A1 | 3/2021 | Carter et al. |

FOREIGN PATENT DOCUMENTS

| | | |
|---|---|---|
| CN | 208172859 | 11/2018 |
| CN | 109658260 A | 4/2019 |
| EP | 3407229 A1 | 11/2018 |
| EP | 3503 038 | 6/2019 |
| JP | 2005050246 A1 | 2/2005 |
| KR | 2005020139 A | 3/2005 |
| WO | WO2003071380 A2 | 8/2003 |
| WO | WO2018022705 A1 | 2/2018 |

OTHER PUBLICATIONS

L. C. Rabelo, A. Jones and Y. Yih, "Development of a real-time learning scheduler using reinforcement learning concepts," Proceedings of 1994 9th IEEE International Symposium on Intelligent Control, Columbus, OH, USA, 1994, pp. 291-296, doi: 10.1109/ISIC.1994.367802. (Year: 1994).*

R. Ho, "Pragmatic Programming Techniques: Characteristics of Machine Learning Model", Feb. 19, 2012, BlogSpot, all pages, horicky.blogspot.com/2012/02/characteristics-of-machine-learning.html (Year: 2012).*

Azmi et al., "Freeman Chain Code Representation in Signature Fraud Detection Based on Nearest Neighbor and ANN Classifiers", 2014, IJIP 8(6), p. 434-454, https://citeseerx.ist.psu.edu/viewdoc/download?doi=10.1.1.736.504&rep=rep1&type=pdf (Year: 2014).*

Calberson et al., "Fraudulent Use of Digital Radiography: Methods to Detect and Protect Digital Radiographs", 2008, JOE, 34(5), p. 530-536, all pages, https://endoexperience.com/documents/FraudulentuseofdigitalrxCalbersonJOE2008.pdf (Year: 2008).*

Ahmed, Musheer, "Augmenting Accountability, Security and Fraud Detection in Health Data Sharing Systems", Georgia Institute of Technology, May 2016.

"8 Rules for E-Signature Security", SIGNiX, 2014.

Reducing Healthcare Fraud in Africa; Genkey Solutions b.v., 2016.

McCormick, John, "AI Helps Spot Dental Fraud", Wall Street Journal, Jan. 24, 2020, available at https://www.wsj.com/articles/ai-helps-spot-dental-fraud-11579861801.

Fracaro et al., "The Sensitivity and specificity of Clinical Assessment Compared with Bitewing Radiology for Detection of Occlusal Dentin Caries", American Academy of Pediatric Dentistry 23:3, Mar. 22, 2001, 204-210.

Markowitz et al. "In Vitro Study of the Diagnostic Performance of the Spectra Caries Detention Aid", The Journal of Clinical Dentistry, 2015,17-22,vol. XXXVI No. 1.

Lee et al. "Diagnosis and Prediction of Periodontally Compromised Teeth Using a Deep Learning-Based Convolutional Neural Network Algorithm", Journal of Periodontal & Implant Science, Apr. 23, 2018,114-123, Apr 48(2).

(56) References Cited

OTHER PUBLICATIONS

Lee et al., "Detection and Diagnosis of Dental Caries Using Deep Learning-Based Convolutional Neural Network Algorithm", Journal of Dentistry, Jul. 25, 2018, 106-111, 77.
Hwang et al. "An Overview of Deep Learning in the Field of Dentistry", Image Science in Dentistry, Mar. 25, 2019, 1-7,49.
Murata et al.,"Towards a Fully Automated Diagnostic System for Orthodontic Treatment in Dentistry," IEEE Computer Society, 2017, 1-8, 13$^{th}$ international conference on eScience.
Shankeeth et al., "Automated detection of third molars and mandibular nerve by deep learning" (pp. 1-7), Jun. 21, 2019.
Young-Jun Yu: "Machine Learning for Dental Image Analysis", Nov. 29, 2016, XP055430578, Retrieved from https://arxiv.org/ftp/arxiv/papers/1611/1611.09958.pdf.
Tian Sukun et al: "Automatic Classification and Segmentation of Teeth on 3D Dental Model Using Hierarchical Deep Learning Networks", IEEE Access, vol. 7, Jul. 15, 2019. pp. 84817-84828, XP011734278, DOI:10.1109/ACCESS.2019.2924262 [retrieved on Jul. 9, 2019].
U.S. Appl. No. 17/075,607, Computer Vision-Based Claims Processing, filed Oct. 20, 2020.
Anoop, Arun, "Image forgery and its detection: A survey", 2015 International Conference on Innovations in Information, Embedded and Communication Systems (ICIIECS), IEEE, Mar. 19, 2015 (Mar. 19, 2015), pp. 1-9.
Calberson FL Get al: "Fraudulent Use of Digital Radiography: Methods to Detect and Protect Digital Radiographs", A Journal of Endodontics, Elsevier, Amsterdam, NL, vol. 34, No. 5, May 1, 2008 (May 1, 2008), pp. 530-536 [retrieved on Mar. 14, 2008] p. 530-p. 532.
International Search Report and Written Opinion for Application No. PCT/US2021/013475, dated Mar. 15, 2021.

\* cited by examiner

| Viewer | | | | |
|---|---|---|---|---|
| FILE  EDIT  VIEW | | | | |
| Code | ↑Tooth | | Surface | |
| D5226 | | | M O D B L | |
| D5213 | | | M O D B L | 502 |
| D2332 | 10 | M | M O D B L | ⚠ Needs Review / Deny / Approve |
| D7210 | 12 | | M O D B L | |
| D7210 | 13 | | M O D B L | |
| D2392 | 18 | M | M O D B L | ⚠ Needs Review |
| D2391 | 18 | M | M O D B L | ⚠ Needs Review |
| D2391 | 19 | | M O D B L | |

FIG. 5

| Viewer | | | | |
|---|---|---|---|---|
| FILE EDIT VIEW | | | | |

| Code | ↑Tooth | | Surface | |
|---|---|---|---|---|
| D5226 | | 🗒 | M O D B L | ⟩ Approved |
| D5213 | | 🗒 | M O D B L | ⟩ Approved |
| D2332 | 10 | 🗒 | M O D B L | ⚠ Outside Guidelines |
| D7210 | 12 | 🗒 | M O D B L | ⟩ Approved |
| D7210 | 13 | 🗒 | M O D B L | ⟩ Approved |
| D2392 | 18 | 🗒 | M O D B L | ⚠ Outside Guidelines |
| D2391 | 18 | 🗒 | M O D B L | ⚠ Likely Denial |
| D2391 | 19 | 🗒 | M O D B L | ⟩ Approved |

FIG. 6

High Priority

| Claim ID | Provider ID | Provider Score | # Weak Evidence | $USD Weak | # Moderate Evidence | $USD Moderate | $ Total Claim | $ Benefit Remaining | |
|---|---|---|---|---|---|---|---|---|---|
| 10503 | 560 | ★★★★★ | 1 | $700 | 2 | $250 | $1,350 | $1,500 | Review > |
| 71352 | 501 | ★★★★★ | 3 | $1,000 | 1 | $25 | $1,400 | $1,000 | Review > |
| 03720 | 401 | ★★★★★ | 2 | $600 | 0 | $0 | $1,200 | $957 | Review > |
| 52871 | 437 | ★★★★★ | 1 | $450 | 0 | $0 | $675 | $800 | Review > |

Low Priority

| Claim ID | Provider ID | Provider Score | # Weak Evidence | $USD Weak | # Moderate Evidence | $USD Moderate | $ Total Claim | $ Benefit Remaining | |
|---|---|---|---|---|---|---|---|---|---|
| 67949 | 432 | ★★★★★ | 0 | $0 | 1 | $250 | $800 | $200 | Review > |
| 28321 | 332 | ★★★★★ | 0 | $0 | 2 | $230 | $776 | $345 | Review > |
| 32387 | 453 | ★★★★★ | 0 | $0 | 1 | $89 | $450 | $1,500 | Review > |

SYSTEMS AND METHODS FOR INSURANCE FRAUD DETECTION

PRIORITY AND INCORPORATION BY REFERENCE

Any and all applications for which a foreign or domestic priority claim is identified in the Application Data Sheet as filed with the present application are hereby incorporated by reference under 37 CFR 1.57.

This application claims benefit of U.S. Provisional Patent Application No. 62/962,828, entitled "SYSTEMS AND METHODS FOR INSURANCE FRAUD DETECTION," filed Jan. 17, 2020, which is hereby incorporated by reference in its entirety.

BACKGROUND

A given health insurance carrier, which may also be referred to as an insurance company or insurance provider, may receive thousands of insurance claims each day. Each insurance claim may be provided to the insurance carrier from a healthcare provider (such as a doctor's or dentist's office, a hospital, etc.), where the claim may indicate a healthcare service rendered by the healthcare provider for a patient who is insured by the given insurance carrier. Given the large volume of claims, it would be prohibitively time consuming for carriers to ensure each claim is thoroughly reviewed by experienced examiners. Instead, the majority of claims submitted to many insurance carriers are not fully evaluated for signs of fraud, waste or abuse.

Healthcare providers may commit health insurance fraud in a number of ways. Such fraud may include billing for services or procedures that were never rendered, charging for a more expensive procedure than what was actually performed, falsifying a patient's diagnosis to justify unnecessary tests or procedures, etc. Insurance fraud is a pervasive problem across medicine and dentistry alike. Dental adjudicators review evidence to evaluate medical necessity with the goal of limiting waste and abuse, but suspicious cases often fail to be flagged.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein.

DETAILED DESCRIPTION

Generally described, aspects of the present disclosure relate to computer-implemented processes and system architectures for automatically identifying fraud, waste or abuse in health insurance claims submitted to insurance companies by healthcare providers (such as by hospitals, doctors, dentists, etc.). Health insurance carriers often receive insurance claims (which may refer to requests for reimbursement submitted to the insurance carrier for health services that the submitter provided to a patient insured by the insurance carrier) that are fraudulent or do not represent a real treatment or service that was actually performed on a patient by the provider. The automated methods of fraud, waste and/or abuse detection described herein may replace or supplement manual review by an examiner of an insurance company, as will be further described below. For example, aspects of the present disclosure for enable the focus of an examiner to be directed to the claims with a highest likelihood of fraud. Given that the volume of claims may prohibit manual review of each and every submitted claim (e.g., a majority of claims may be approved without review due to shortage of examiner or other reviewing personnel), ensuring that the claims reviewed are those most likely to have fraud or abuse issues may result in a significantly higher number of fraudulent claims being identified relative to prior art methods. In some embodiments of the present disclosure, certain insurance claims may be automatically approved or denied without manual review based on an automatically determined confidence value, as will be discussed below.

Aspects of the present disclosure relate to machine learning-based approaches to analyzing images that are provided in health insurance reimbursement claims for evidence of insurance fraud. These images may be image files that a healthcare provider attaches or includes in their insurance claim as evidence of the health service that they claim they performed for a patient. In some embodiments, a machine learning model may be trained to learn to detect that a very similar x-ray, radiograph, medical form, doctor's note scan, practice management software screenshot, or other image has been submitted in multiple health insurance claims, which would be a sign of fraud (e.g., a doctor took one radiograph for one patient, but has re-submitted the same radiograph or a modified version of the same radiograph to support a claim for a second patient). A machine learning model may be trained to identify similar images that are not exactly the same, but where it appears that the submitter edited one image to make the second image (e.g., placed a different patient name over the same medical image). As will be further discussed below, the detection of identical images or near-identical images that may be associated with fraudulent claims may be based in part on generating a signature for each image submitted to one or more insurance carriers, such that images likely to be considered nearly identical from a fraud perspective will share the same or similar signature as each other.

In some embodiments, the machine learning approaches to fraud detection discussed herein may further include utilizing computer vision techniques to identify any of various pathologies, conditions, anatomies, anomalies or other medical issues depicted in a radiograph image, such as using systems and methods disclosed in U.S. patent application Ser. No. 16/562,286, entitled SYSTEMS AND METHODS FOR AUTOMATED MEDICAL IMAGE ANALYSIS, filed Sep. 5, 2019 (hereinafter "the '286 application"), the entirety of which is hereby incorporated by reference herein. In some embodiments, the presence of potential fraud, waste or abuse in a claim may be based at least in part on a determination that conditions or features associated with one or more treatment codes submitted in an insurance claim are not identified in the claim's supporting radiograph image(s) using machine learning models such as those disclosed in the '286 application.

Fraud detection solutions described herein may include creating a fingerprint or signature for each claim that enables the system to identify where and when a duplicate or near-duplicate claim was last seen. In some embodiments, by automatically flagging or identifying such similar previously submitted claims, insurance carriers can more easily recognize or be alerted to both clerical errors and potential fraud, waste or abuse present in submitted claims. This may occur as claims are submitted (e.g., before the submitter is reimbursed or paid out by the carrier), or may occur on a batch basis for previously submitted claims as part of an audit or other claim review process.

Figure 1:
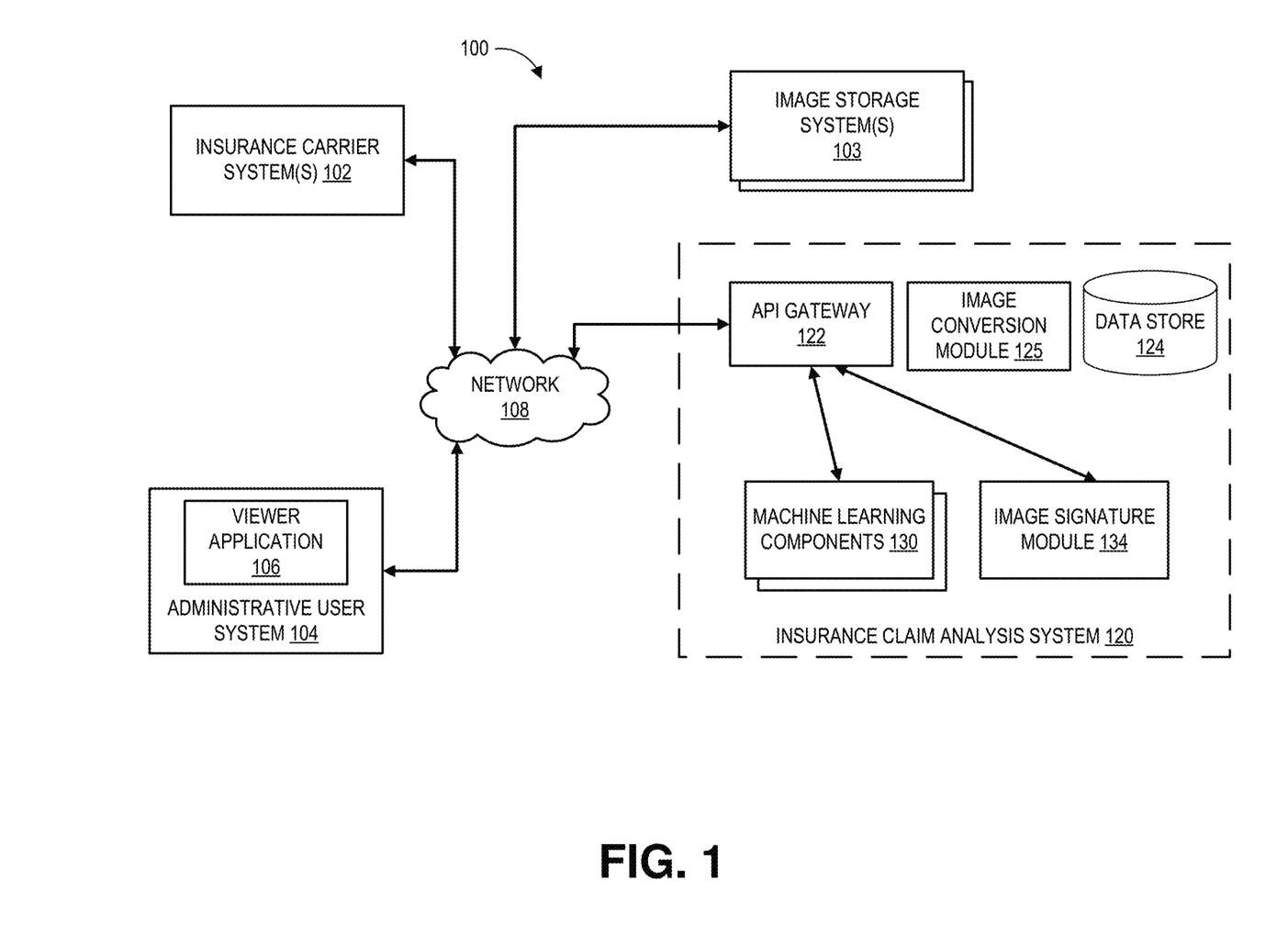
FIG. 1 illustrates a networked computing environment suitable for implementing features of an insurance claim analysis system, according to some embodiments.

FIG. 1 illustrates a networked computing environment 100 suitable for implementing features of an insurance claim analysis system, according to some embodiments. The environment 100 includes a network 108, one or more insurance carrier systems 102, one or more image storage systems 103, an administrative user system 104, and an insurance claim analysis system 120. To simplify discussion and not to limit the present disclosure, FIG. 1 illustrates only one insurance carrier system 102, though multiple insurance carrier systems may be present in many embodiments. For example, the insurance claim analysis system 120 may be configured to provide claim analysis for a number of different insurance carriers, and may identify duplicate claims or other potentially conflicting claims across carriers (e.g., identifying that a claim submitted to a first insurance carrier appears to be potentially fraudulent based on a claim previously submitted to a second insurance carrier).

The administrative user system 104 may be operated by a user associated with either the operator of the insurance claim analysis system 120 or an insurance carrier (such as an operator of the insurance carrier system 102). For example, the viewer application 106 may be installed on one or more computer systems operated by a claims examiner employed by an insurance carrier, where the viewer application may present claim review user interfaces such as those that will be described with respect to FIGS. 4-7 below. In other embodiments, functionality described herein as being provided by the insurance carrier system and the administrative user system may be implemented within a single computing system or device associated with a given insurance carrier.

The insurance claim analysis system 120 can include API gateway 122, one or more data stores 124, an image signature module 134, and machine learning components 130. The machine learning components may include multiple pre-processing classifiers, machine learning models, and post-processors, such as those further discussed in the '286 application. As will be discussed below, the API gateway 122 can communicate with the systems 102, 103 and/or 104 (e.g., using a network 108, such as the Internet) to receive various information or files (such as claim information, images, etc.) associated with insurance claims and coordinate subsequent image processing and analysis by the machine learning components 130. Although only one network 108 is illustrated, multiple distinct and/or distributed networks may exist. The various systems and other components illustrated in FIG. 1, including interactions or communications between them, will be described in more detail below with respect to FIG. 2.

The insurance carrier system 102 illustrated in FIG. 1 may include hardware and software components for establishing communications over a communication network 108. For example, the insurance carrier system 102 may be equipped with networking equipment and network software applications (for example, a web browser and/or a proprietary application or API interface associated with an operator of the insurance claim analysis system 120) that facilitates communications via one or more networks (for example, the Internet, an intranet or a virtual private network). Each insurance carrier system 102 may have varied local computing resources such as central processing units and architectures, memory, mass storage, graphics processing units, communication network availability and bandwidth, and so forth. Further, the insurance carrier system 102 may include any type of computing system. For example, the insurance carrier system 102 may include one or more desktop computers, laptop computers, and/or servers operated in association with a medical practice, in some embodiments. The insurance carrier system 102 can include a data store (not illustrated) that may store various insurance claim information. Such a data store as well as the data store 124 associated with the insurance claim analysis system may employ various security and privacy protocols known in the art for storage of medical data, including Health Insurance Portability and Accountability Act ("HIPAA") compliance.

Figure 2:
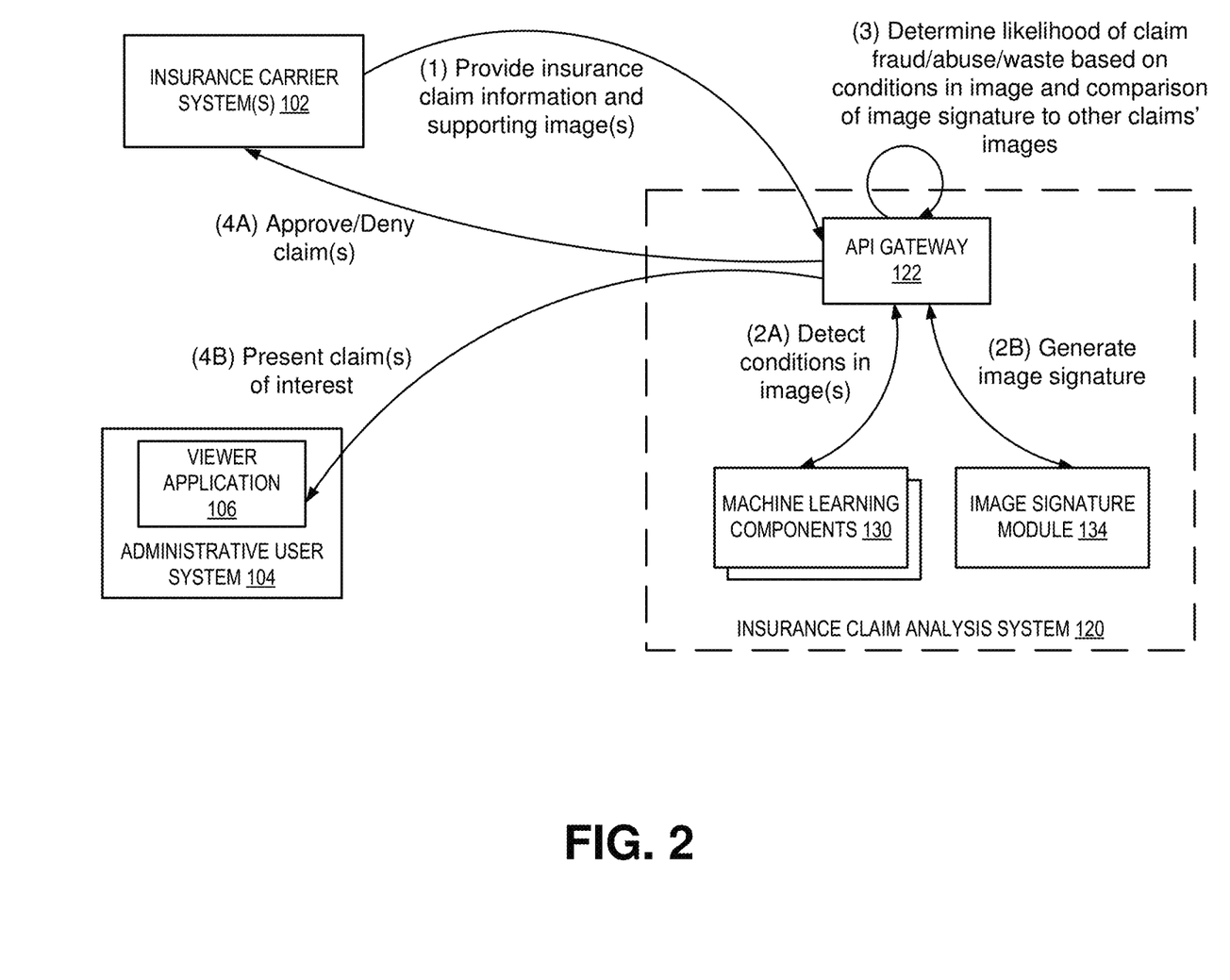
FIG. 2 illustrates example data flow within the networked computing environment of FIG. 1.

FIG. 2 illustrates example data flow within the networked computing environment of FIG. 1. For ease of illustration, the data flow of FIG. 2 does not specify whether individual communications between illustrated components or systems are over a network or are local within a single computing system or device. While one example network arrangement is illustrated in FIG. 1 and described above, it will be appreciated that components or subsystems illustrated as part of a single computing system in FIG. 1 may instead be remotely located relative to each other. Similarly, other systems or components illustrated as in network communication with each other in FIG. 1 may in some embodiments be operated together on a single computing system or may be in direct local communication with each other rather than communicating over a network.

The illustrative data flow begins at step (1) with an insurance carrier system 102 providing insurance claim information and supporting image data to the insurance claim analysis system 120, such as via the API gateway 122. For example, the insurance carrier system may send an API request for the insurance claim analysis system 120 to analyze or process one or more insurance claims that have been submitted to the carrier from a healthcare provider. In some instances, a set of claims may be provided in a batch process, while in other instances an individual claim may be sent (e.g., an individual claim may be forwarded to the insurance claim analysis system 120 shortly after or in near real time with respect to a time at which the claim is initially received by the carrier). As discussed above, the claim information may include supporting imagery that a doctor, dentist or other healthcare provider has included with their claim submission to provide evidence or documentation to the carrier of the medical service provided, such as an image file depicting a radiograph, a medical form, a scan of a doctor's note, a practice management software screenshot, or other image.

For each received claim, the API gateway 122 may then provide the corresponding received image(s) and optionally other claim information to both the machine learning components 130 and image signature module 134, which may occur sequentially or in parallel at steps (2A) and (2B). The results of processing the images and other claim information by the machine learning components 130 at step (2A) may result in detection of one or more conditions, diagnoses, or other medical data depicted, present or referenced in the image(s), as will be discussed further below. The image signature module 134 at step (2B) may generate a signature or fingerprint for the image(s) and/or claim as a whole for comparison to signatures or fingerprints from other claims in order to assess potential duplicates or near duplicates, as will be further discussed below. Based on the information determined at steps (2A) and (2B), the API gateway 122 or other component of the insurance claim analysis system 120 may determine a likelihood of claim fraud, waste or abuse at step (3), as will be further discussed with respect to FIG. 3.

For example, the insurance claim analysis system may identify a potential instance of fraud when there is a mismatch between a condition that a doctor indicated was treated or diagnosed as part of a given claim and the machine learning components' assessment of whether that condition is depicted in a supporting radiograph submitted with the claim. As another example, the insurance claim analysis system may identify a potential instance of fraud based on a determination that the image signature generated for an image included with the claim submission matches or is a near match to an image signature of another image previously submitted with one or more prior claims (which may indicate, for example, that a doctor is representing that a given radiograph showing the presence of a given medical condition was captured for a certain patient on a given day, when it was actually a radiograph captured on a different day and/or for a different patient, for which the doctor submitted a separate request for insurance reimbursement).

In some embodiments, the API gateway 122 may then send an API response to the insurance carrier system 102 at step (4A), where the response may include an approval or denial recommendation for the submitted claim(s) based on the assessed likelihood of fraud, waste or abuse. The insurance carrier system 102 may be configured, in some instances, to automatically approve or deny certain claims based on the response (e.g., if the likelihood or score falls above an approval threshold or below a denial threshold, respectively). In some embodiments, the API gateway may, at step (4B), send information to the administrative user system 104 that causes presentation in the viewer application 106 of one or more user interfaces that enable the user (such as an insurance claims examiner) to review and approve/deny individual claims based at least in part on the automated assessment performed by the insurance claim analysis system 120. These and other features of the present disclosure will be further described below with reference to additional figures.

Figure 3:
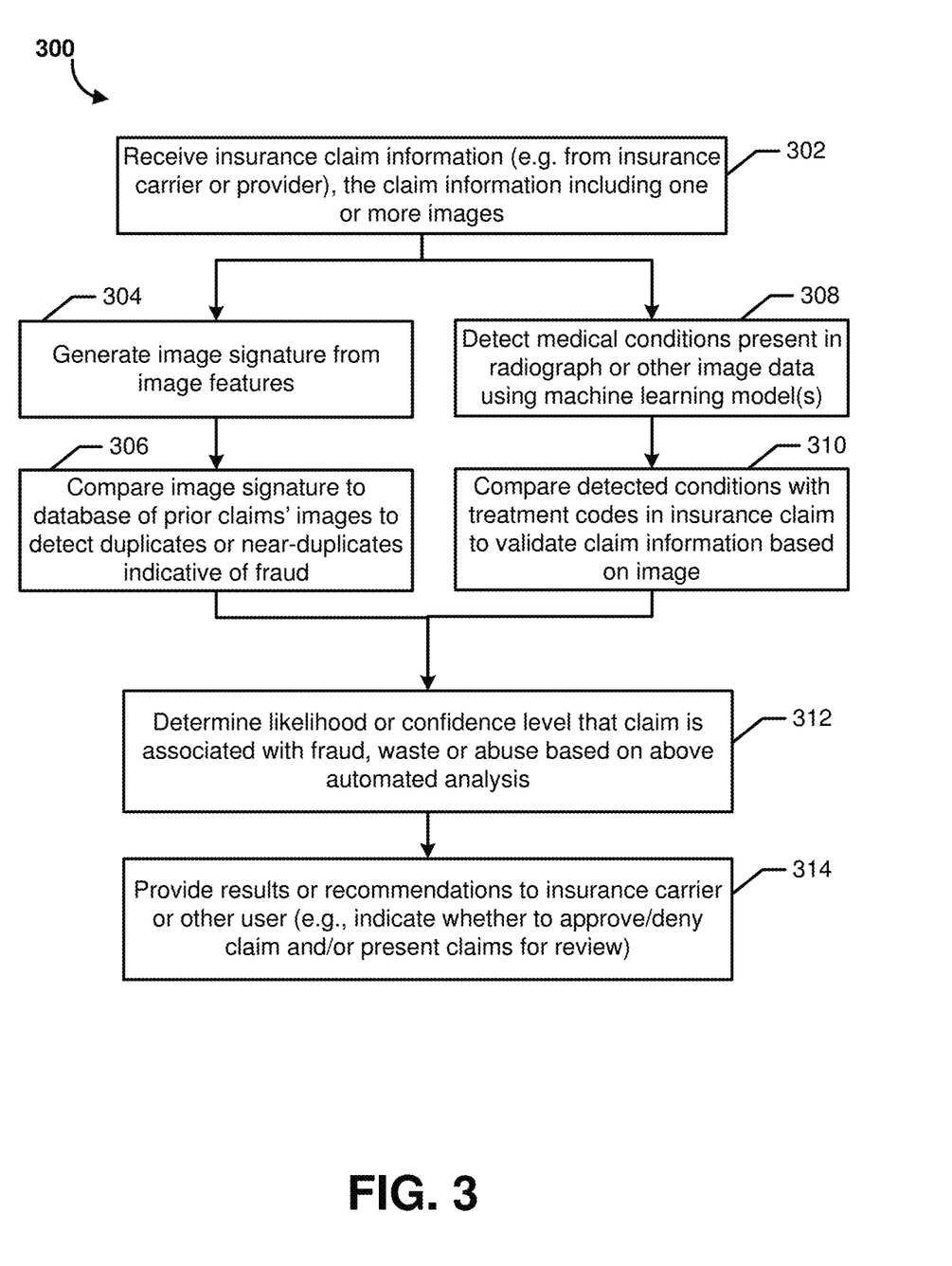
FIG. 3 is a flow diagram of an illustrative method for detecting a potentially fraudulent insurance claim, according to some embodiments.

FIG. 3 is a flow diagram of an illustrative method 300 for detecting a potentially fraudulent insurance claim, or an insurance claim with other signs of waste or abuse, according to some embodiments. The illustrative method 300 may be performed by the insurance claims analysis system 120, in some embodiments.

The illustrative method 300 begins at block 302, where the insurance claims analysis system 120 may receive insurance claim information, such as from insurance carrier system. As discussed above, the claim information may include one or more images, such as digital image files that depict radiographs, doctor's notes (e.g., a photograph or scan of a doctor's handwritten notes, or a screenshot of digitally written notes), practice management software application screenshots or exports (e.g., an export in an image file format or PDF format), prescriptions, patient charts, test results, filled in medical forms, and/or other visual imagery. The claim information received or obtained at block 302 may further include various claim information or metadata, which may be in a structured form (e.g., field names and corresponding values or entries). Such claim information may include, for example, patient data, a unique identifier for the claim, one or more treatment codes, healthcare provider information, time and date information, and/or other data known in the field of insurance claim processing.

The method 300 may then proceed to blocks 304 and/or to block 308 to begin analysis of the claim information and image(s). While block 304 is implemented prior to block 306, and block 308 is implemented prior to block 310, the pair of blocks 304 and 306 may be implemented either before, after or in parallel with the pair of blocks 308 and 310. In some embodiments, the likelihood of fraud (determined at block 312 discussed below) may be based on results of only one of the blocks 306 or 310 (e.g., based only on image signature comparisons or only on medical condition analysis), or may be based on both. Thus, it will be appreciated that there are embodiments in which blocks 304 and 306 may not be implemented, and other embodiments in which blocks 308 and 310 may not be implemented.

At block 304, the insurance claims analysis system 120 may generate an image signature (which may be considered an image fingerprint in some embodiments) for either each individual image associated with the claim or for a set of images associated with the claim. In some embodiments, this may first include pre-processing composite imagery, such as using a machine learning model to extract relevant child images if multiple are present in a parent image. The insurance claims analysis system 120 may generate or extract features for the image(s) using one or more previously trained machine learning models (training will be further discussed below). The features may generally be extracted using mathematical transformations of the image data and/or as the features determined at one or more layers of a machine learning model. Additional details regarding such transformations and machine learning models will be further discussed below. The signature(s) may then be stored in a database for future comparisons to images associated with other insurance claims.

Next, at block 306, the insurance claims analysis system 120 may compare the generated image signature(s) for the currently analyzed claim to a database of prior claims' images to detect duplicates or near-duplicates indicative of fraud. As will be further discussed below, the signatures may be generated in manner whereby an image that has been modified so as not to appear identical to a prior image (e.g., a radiograph, prescription, etc. in which an original patient name has been changed or an image has been cropped or rotated) will nonetheless have a matching or close signature to the prior image (e.g. based on Euclidian distance between the signatures, in one embodiment). If duplicate or near duplicate images are found for the currently analyzed image in in the database of claims, the system may flag the relevant image and/or claim as potentially fraudulent.

At block 308 (which may be performed before or after blocks 304 and/or 306, as discussed above), the insurance claims analysis system 120 may detect one or more pathologies, conditions, anatomies, anomalies or other medical issues depicted in a radiograph image, such as using machine learning systems and methods disclosed in the '286 application referenced above. At block 310, the insurance claims analysis system 120 may compare the detected condition(s) or other medical issue(s) depicted in the radiograph image with one or more treatment codes that were submitted in the claim information. This may include consulting a lookup table or mapping data that maps treatment codes to classification labels that the machine learning models are configured to predict from radiograph image data. The presence of potential fraud may be flagged by the system if the conditions or features associated with one or more treatment codes submitted in an insurance claim are not identified in the claim's supporting radiograph image(s) using machine learning models such as those disclosed in the '286 application.

For example, if a dentist submits an insurance claim containing a treatment code for a root canal, but the machine learning model does not identify the presence of a root canal in the supporting radiograph provided by the dentist to the insurance carrier, the system may flag the claim for further review by a claims examiner. An example in which the system may recommend approval of a claim may be (assuming that no duplicate image signatures were found) that an instance of caries (approaching or into pulp) was detected by the machine learning model(s) and the claim includes a treatment code for crown installation, which the system may be configured to recognize is an appropriate mapping between treatment code and radiograph condition.

At block 312, the insurance claims analysis system 120 may determine a likelihood or confidence level (such as a numeric score) that the analyzed claim is associated with fraud, waste or abuse based on the above-discussed automated analysis of blocks 306 and/or 310. This likelihood, confidence level or score may be determined in a number of ways depending on the embodiment. For example, certain flagged instances discussed above may lead to an automatic classification of potential fraud (e.g., a high likelihood or score). In other embodiments, various weights may be assigned to different factors, rules may be applied, and/or machine learning models may be trained to generate the likelihood of fraud from the various information and comparisons discussed above. At block 314, the results of the analysis may be used to generate recommendations to a user of whether to approve or deny the claim, generate an automated approval or denial, and/or present claims to a user for review. Recognized relationships between different claims (e.g. relationships between claims having signature similarity and/or various other associated metadata in common) may also be stored in the claim database to group sets of claims that follow patterns of similarity or that are likely to include one or more fraudulent claims in view of one another. Example claim review user interfaces will be discussed below with respect to FIGS. 4-7.

Certain methods for image signature generation will now be described with respect to certain embodiments, but are not intended to be limited. As mentioned above, the signature for an image may be generated based on extracted features of the image, where the extracted features may be based on mathematical transformation of the image data and/or may be the features generated at one or more layers of a machine learning model. In some embodiments, feature extraction may include methods such as scale and rotation-invariant descriptors (e.g., SURF, PHOG, GLOH, etc.). In some embodiments, the features for generating a signature may be based on feature maps from one of more convolutional layers in a convolutional neural network (e.g., VGG-16, ResNet, DenseNet, an encoder branch of Autoencoder, etc.), which may rely on supervised or unsupervised learning. Transformations applied may include subsampling of raw image intensities, and/or re-representation of the image by one or more transformations (such as the Discrete Cosine Transform (DCT)).

In some embodiments, the machine learning model(s), such as a convolutional neural network, employed in the feature extraction process may be trained on general imagery, trained on claim-specific imagery, and/or trained on artificially generated near-duplicates that are generated based on transformations known to be present prior instances of fraud, waste or abuse of insurance claims. In embodiments in which artificially generated near-duplicates are employed in training, these near duplicates may be created from base images by applying one or more transformations such as versions of the following that are consistent with prior instances of fraud, waste or abuse: rotation, illumination perturbations, insertion or removal of text, image superimposition, cropping, and/or other transformation found to commonly occur in instances of fraudulent or near duplicate claim submissions.

Once the extracted features are determined for an image, the signature may be generated, in some embodiments, using a hashing function. For example, a hashing function may be used to compress the image features into a fixed-length signature or hash (which may be considered feature hashing). The feature hashing may include calculating the average feature and then thresholding each feature element by its proximity to the average. As another example, the feature hashing may include assigning a hash value per element using the sign of the feature (e.g. 0 for negative, 1 for positive). However, it will be appreciated by one of ordinary skill in the art that any of a wide variety of hashing methods or other algorithms may be employed to generate the signature from the extracted image features.

FIGS. 4-7 depict illustrative user interfaces that present information regarding insurance claims and enable a user to make selections, according to some embodiments. The user may be, for example, an insurance claims examiner, clinician or auditor, in some instances. The user interfaces may be presented for display, in some embodiments, by the viewer application 106 of the administrative user system 104 based in part on information generated by the insurance claim analysis system 120.

Figure 4:
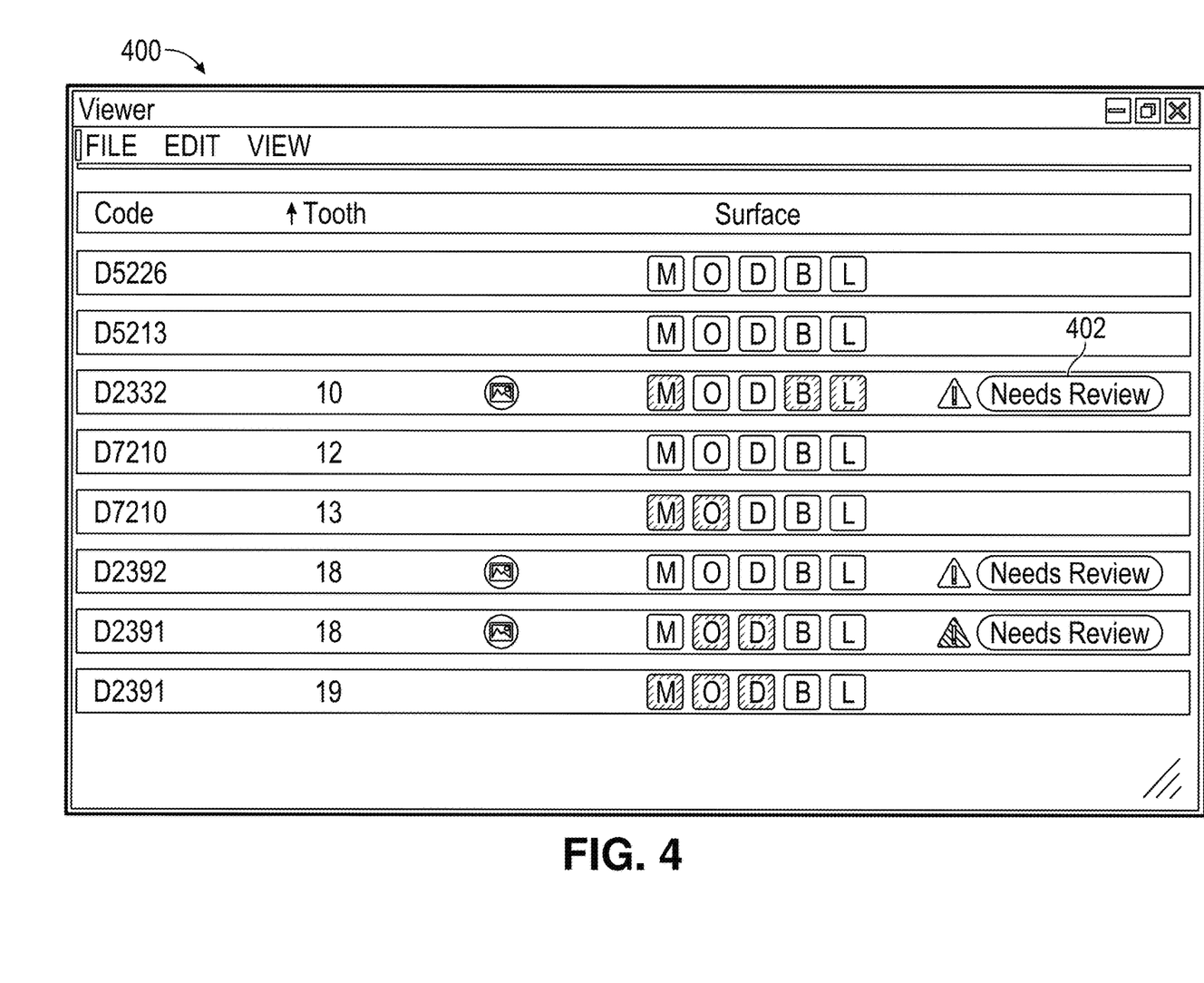
FIGS. 4-7 depict illustrative user interfaces that present information regarding insurance claims and enable a user to make selections, according to some embodiments.
Figure 5:
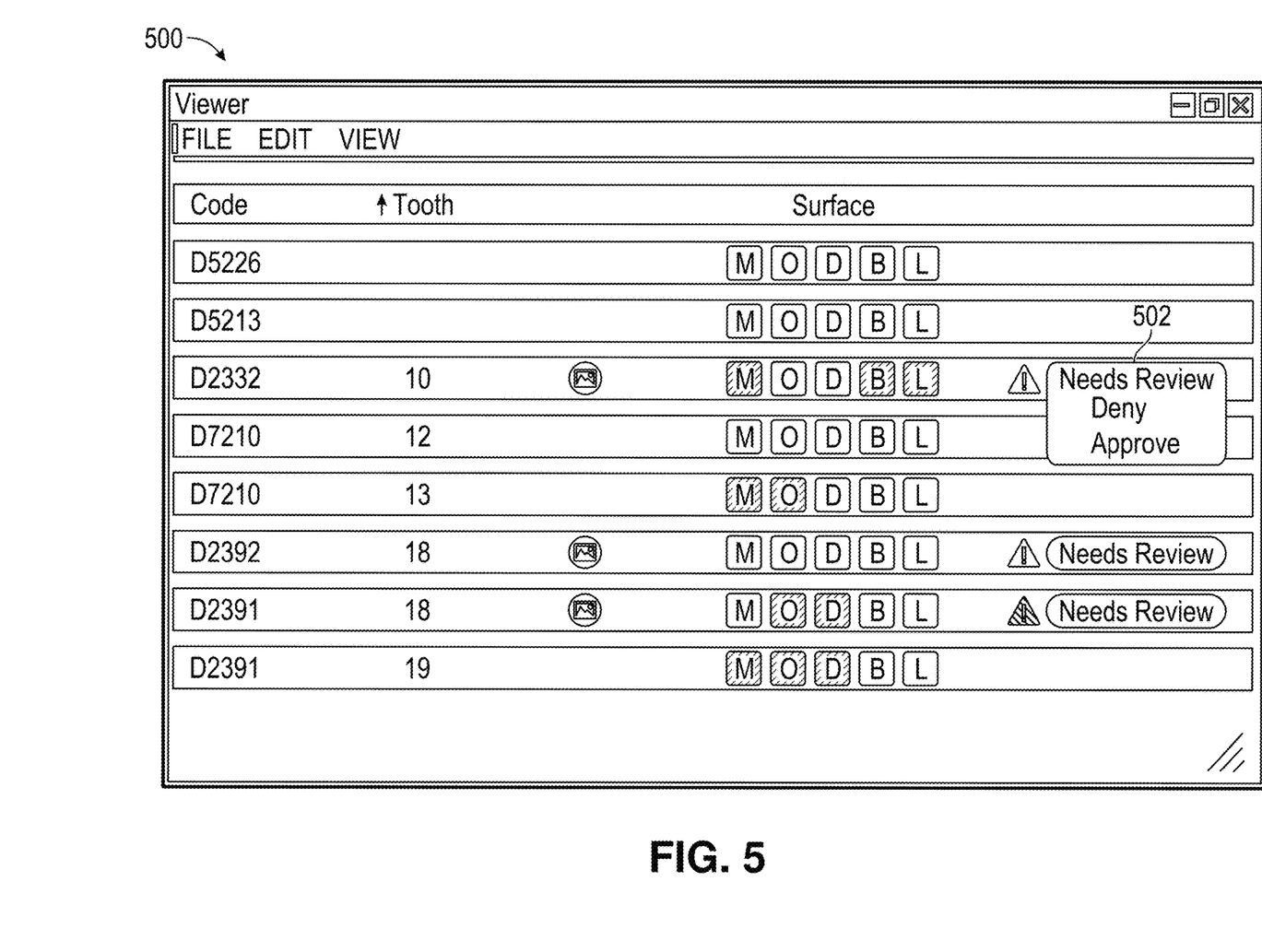
Figure 6:
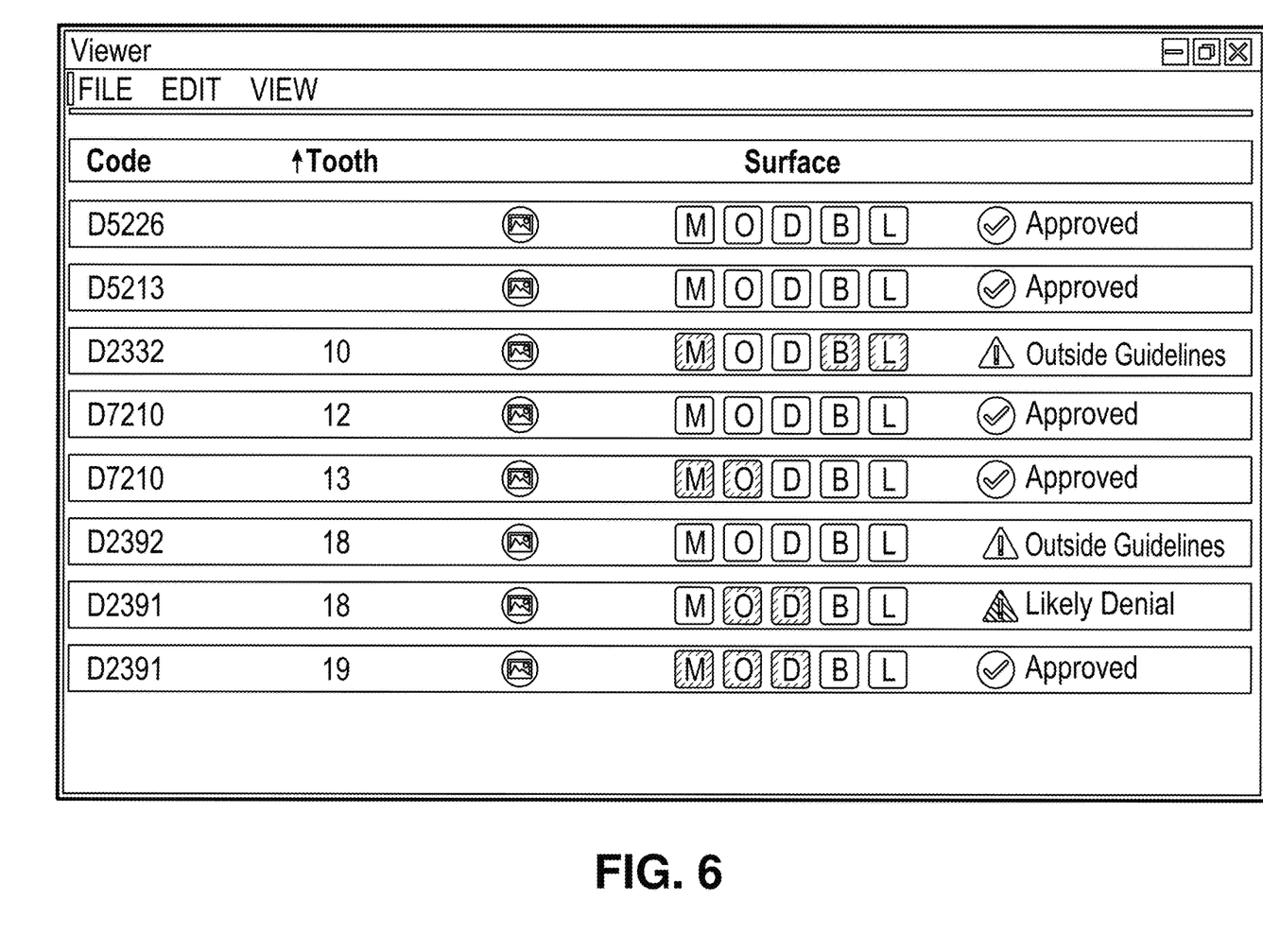

As illustrated in FIG. 4, the user interface 400 may be considered an example claims approval interface. The displayed rows may each correspond to a different claim that has been submitted for approval. The "code" column may include a code value that is part of the claim as originally assigned by the insurance carrier, for instance. The "tooth" column may include a tooth number that was output by the machine learning models discussed above (such as those in the '286 application) based on tooth detection performed on a radiograph image, for instance. The "tooth" column entry, in other embodiments, may additionally or alternatively be populated based on claim information, such as claim information received from the insurance carrier. The user may select the image icons in the next column to view the corresponding image. The icons in the "surface" column may be additional information from the insurance claim. The claim data that the insurance claim analysis system 120 has flagged as needing review (e.g., items potentially associated with fraud, waste or abuse) include a "needs review" selectable option, such as option 402. If the user selects option 402, the user interface display may be updated as shown in user interface 500 of FIG. 5 to include drop-down options to approve or deny the claim (as shown at 502). FIG. 6 then illustrates an interface displaying the status of a number of claims as "approved" and another as "likely denial." These statuses may have been automatically applied by the insurance claim analysis system 120 in some embodiments, or may have been the result of manual selection by the user.

Other user interfaces similar to those described above may further include functionality for the user to enter various forms of claim queries, flag images or claims, and/or bookmark images or claims. In some embodiments, the user may toggle between browse or query modes, where a query mode may enable the user to enter queries to search the claim database (such as using SQL or similar commands). For example, the user may be able to search for all matches for a particular image signature (e.g., see that a given image has been submitted in duplicate or near duplicate form across ten different claims), filter or sort the displayed claims by treatment code or other field, etc.

Figure 7:
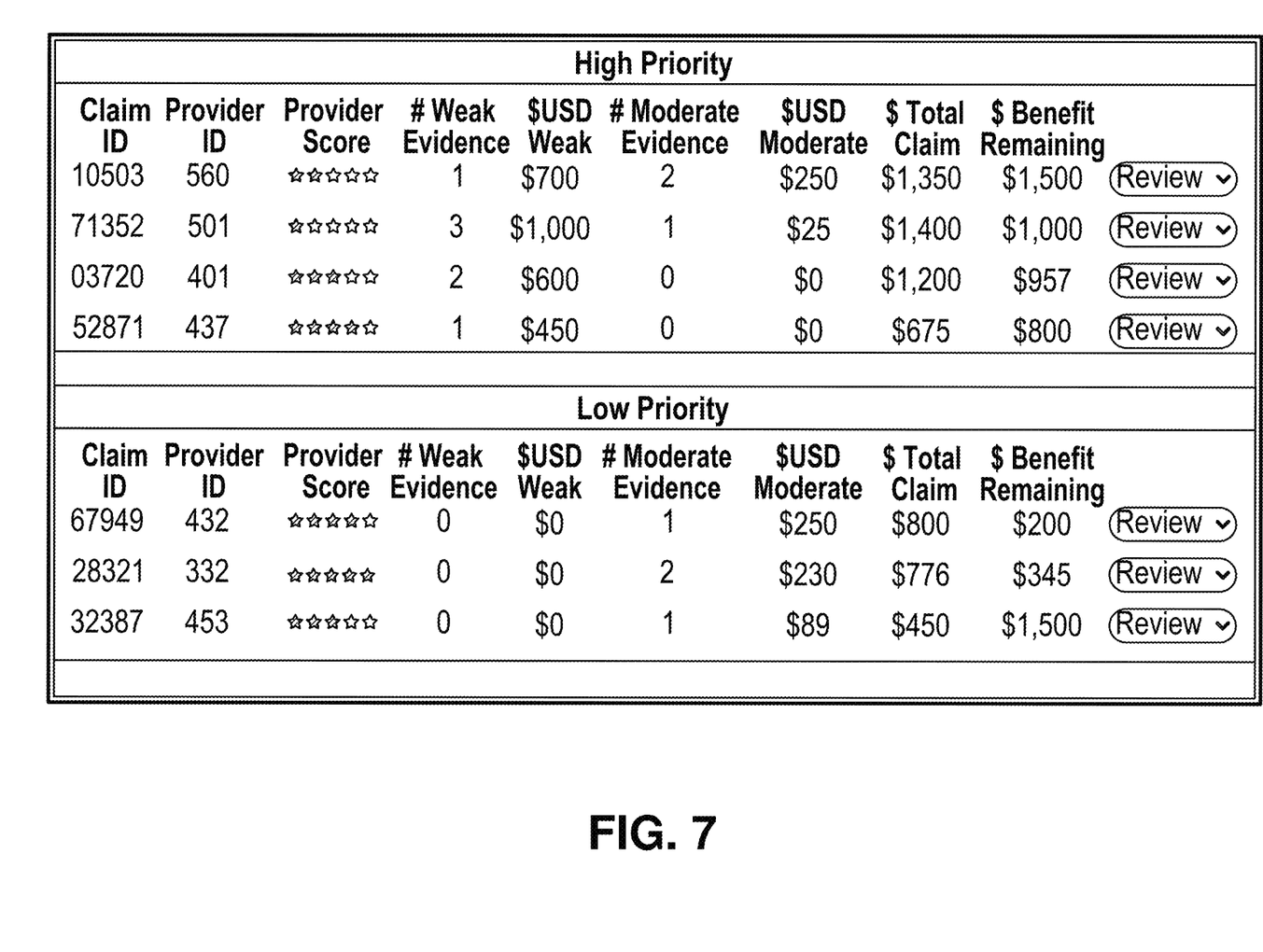

FIG. 7 illustrates an example user interface for claim triaging in which a user may quickly separate claims for review into high and low priority based on the automated assessments made by the insurance claim analysis system 120. For example, the claims may be automatically ranked or sorted based on their predicted likelihood of denial (such as due to potential fraud, waste or abuse) as determined by the insurance claim analysis system 120. As illustrated, the displayed information for the high priority claims may include data such as the number of instances of weak evidence and the total dollars associated with the weak evidence. In this manner, if the user only has time to manually review a small subset of the total claims that have been submitted, the user may focus on the high value claims to lower the carrier's potential losses relative to including these high value claims in an auto-approved bucket (as may occur in prior art methods).

Figure 8:
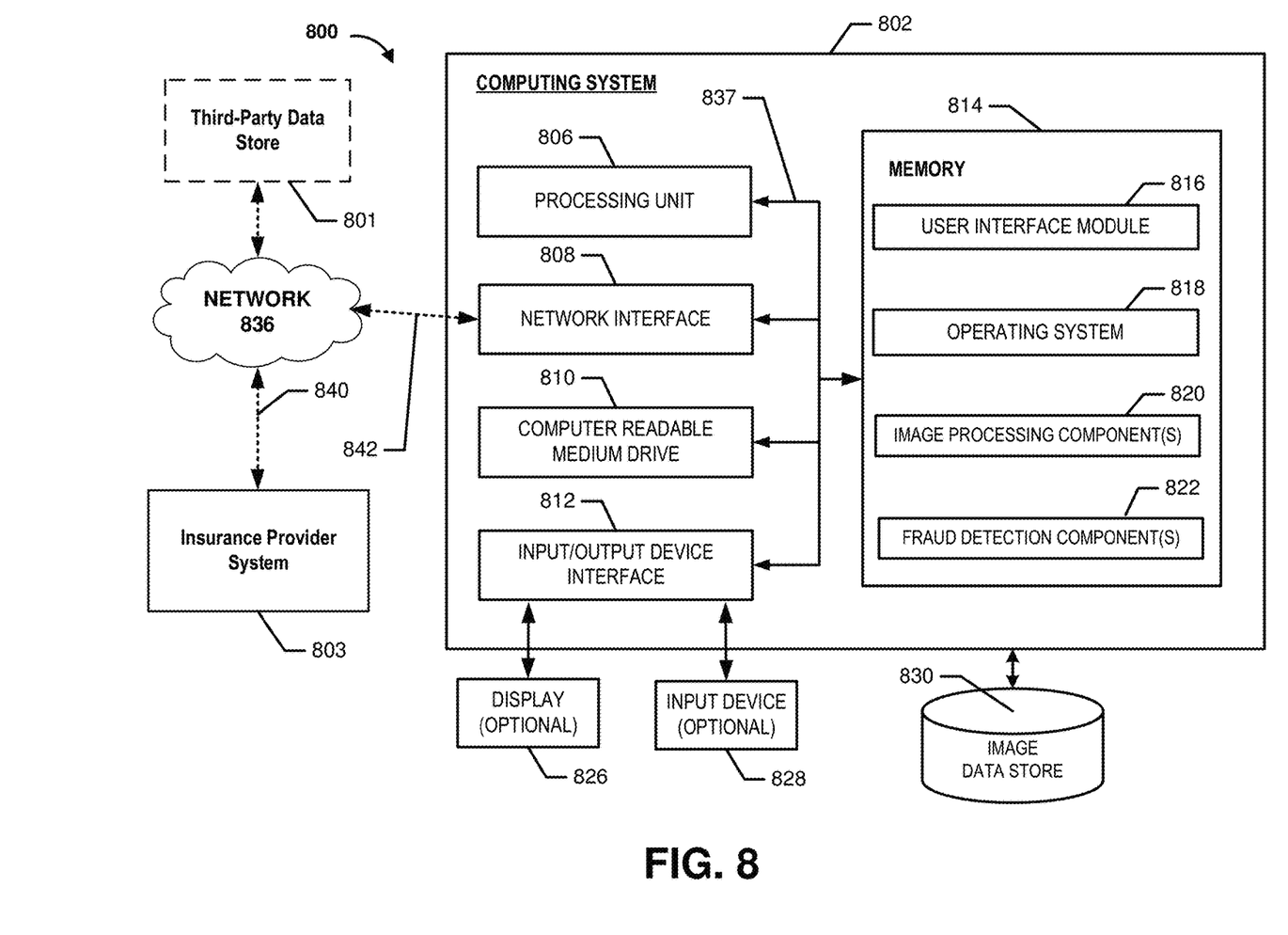
FIG. 8 is a system block diagram of a computing environment suitable for use in various embodiments of the present disclosure.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. It is not necessary, however, that all of these generally conventional elements be shown in order to provide an enabling disclosure. In some embodiments, the computing system 802 may be an example of what is referred to as the insurance claim system above, though an insurance carrier system and/or administrative user system described above may include one or more similar components, in some embodiments.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more image processing components 820 and fraud detection components 822, which may be executed by the processing unit 806 to perform operations according to various embodiments described herein. The modules 820 and/or 822 may access the image data store 830 in order to retrieve and analyze image data and generate other associated data as described herein. Other data stores, such as a claims data store, may also be present in some embodiments. The data store(s) may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks. In the example illustrated in FIG. 8, the network interface 808 may be in communication with an insurance provider system 803 via the network 836, such as the Internet. In particular, the computing system 802 may establish a communication link 842 with a network 836 (e.g., using known protocols) in order to send communications to the computing system 803 over the network 836. Similarly, the computing system 803 may send communications to the computing system 802 over the network 836 via a wired or wireless communication link 840. In some embodiments, the computing system 802 may additionally communicate via the network 836 with an optional third-party data store or data service 801, which may be used by the computing system 802 to retrieve remotely stored image files, claims data, and/or other information, data or files.

Those skilled in the art will recognize that the computing systems 802 and 803 may be any of a number of computing systems including, but not limited to, a laptop, a personal computer, a mobile phone, a smartphone, a tablet computer, another wireless device, a set-top or other television box, one or more servers, and the like. The system 803 may include similar hardware to that illustrated as being included in computing system 802, such as a display, processing unit, network interface, memory, operating system, etc.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or through multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
   memory; and
   a processor in communication with the memory and configured with processor-executable instructions to perform operations comprising:
      obtaining, for a first insurance claim, insurance claim information and at least a first radiograph image associated with the first insurance claim, wherein the first radiograph image has been submitted by a healthcare provider to an insurance carrier as supporting evidence of a medical service indicated in the insurance claim information as having been performed by the healthcare provider;
      generating a digital signature representing the first radiograph image, wherein the digital signature is generated based at least in part on image data within the first radiograph image, wherein generating the digital signature representing the first radiograph image comprises:
  implementing a feature extraction process with respect to the image data within the first radiograph image to extract a plurality of features of the image data, wherein the feature extraction process comprises at least one of: (i) providing the image data within the first radiograph image as input to a convolutional neural network and extracting the plurality of features of the image data from one or more layers of the convolutional neural network, or (ii) applying mathematical transformations to image intensity data within the first radiograph image; and
  applying a hashing function to at least a subset of the plurality of features of the image data to generate the digital signature representing the first radiograph image;
comparing the digital signature generated for the first radiograph image to previously generated digital signatures of other images that have been submitted in association with insurance claims other than the first insurance claim, wherein the previously generated digital signatures have been generated using the feature extraction process and the hashing function with respect to image data of the other images;
identifying a match between the digital signature generated for the first radiograph image submitted for the first insurance claim and one or more of the previously generated digital signatures of other images submitted in association with the insurance claims other than the first insurance claim;
determining, based on the match identified between the digital signature and the one or more of the previously generated digital signatures, that the first radiograph image submitted for the first insurance claim is a duplicate of at least one radiograph image previously submitted to the insurance carrier for a different insurance claim other than the first insurance claim;
determining that the first insurance claim is associated with potential fraud based at least in part on the identified match between the digital signature and the one or more of the previously generated digital signatures; and
based at least in part on the determining that the first insurance claim is associated with potential fraud, generating at least one of (a) a recommendation for the insurance carrier to deny the first insurance claim, or (b) user interface data that enables a user to review whether to approve or deny the first insurance claim.

2. The computer system of claim 1, wherein the operations further comprise:
using one or more machine learning models, detecting one or more medical conditions present in the first radiograph image; and
comparing the one or more medical conditions present in the first radiograph image with one or more treatment codes included in the insurance claim information,
wherein the recommendation for the insurance carrier to deny the first insurance claim is based in further part on whether the one or more treatment codes are associated with the one or more medical conditions detected in the first radiograph image.

3. The computer system of claim 1, wherein the first insurance claim is determined by the computer system to be associated with potential fraud regardless of whether any previous images having the one or more previously generated digital signatures have been identified as associated with fraud prior to the comparing of the digital signature generated for the first radiograph image to the previously generated digital signatures.

4. The computer system of claim 1, wherein the feature extraction process comprises providing the image data within the first radiograph image as input to the convolutional neural network and extracting the plurality of features of the image data from the one or more layers of the convolutional neural network.

5. The computer system of claim 1, wherein the comparing of wherein the operations further comprise:
determining that the first insurance claim is associated with potential fraud based at least in part on the comparing of the digital signature generated for the first radiograph image to the previously generated digital signatures indicating that a radiograph depicted in the first radiograph image is not a radiograph first captured in association with the first insurance claim.

6. The computer system of claim 1, wherein determining that the first insurance claim is associated with potential fraud includes determining a likelihood that the first insurance claim is associated with one or more types of fraud associated with one or more of: (a) the healthcare provider billing for services or procedures that were not rendered by the healthcare provider, (b) the healthcare provider billing for a more expensive procedure than was actually performed by the healthcare provider, or (c) the healthcare provider falsifying a diagnosis of a patient to justify unnecessary tests or procedures.

7. A computer-implemented method comprising:
as implemented by one or more computing devices configured with specific executable instructions,
  obtaining, for a first insurance claim, insurance claim information and at least a first image associated with the first insurance claim, wherein the first image has been submitted by a healthcare provider to an insurance carrier as supporting evidence of a medical service indicated in the insurance claim information as having been performed by the healthcare provider;
  generating a digital signature representing the first image, wherein the digital signature is generated based at least in part on image data within the first image, wherein generating the digital signature representing the first image comprises:
    implementing a feature extraction process with respect to the image data within the first image to extract a plurality of features of the image data, wherein the feature extraction process comprises at least one of: (i) providing the image data within the first image as input to a convolutional neural network and extracting the plurality of features of the image data from one or more layers of the convolutional neural network, or (ii) applying mathematical transformations to image intensity data within the first image; and
    applying a hashing function to at least a subset of the plurality of features of the image data to generate the digital signature representing the first image;
  comparing the digital signature generated for the first image to previously generated digital signatures of other images that have been submitted in association with insurance claims other than the first insurance claim, wherein the previously generated digital signatures have been generated using the feature extraction process and the hashing function with respect to image data of the other images;

identifying a match between the digital signature generated for the first image submitted for the first insurance claim and one or more of the previously generated digital signatures of other images submitted in association with the insurance claims other than the first insurance claim;

determining, based on the match identified between the digital signature and the one or more of the previously generated digital signatures, that the first image submitted for the first insurance claim is a duplicate of at least one image previously submitted to the insurance carrier for a different insurance claim other than the first insurance claim;

determining that the first insurance claim is associated with potential fraud based at least in part on the identified match between the digital signature and the one or more of the previously generated digital signatures; and based at least in part on the determining that the first insurance claim is associated with potential fraud, generating at least one of (a) a recommendation for the insurance carrier to deny the first insurance claim, or (b) user interface data that enables a user to review whether to approve or deny the first insurance claim.

8. The computer-implemented method of claim 7, wherein the first image depicts at least one radiograph.

9. The computer-implemented method of claim 7, wherein the first image depicts at least a first radiograph, and wherein the method further comprises:

using one or more machine learning models, detecting one or more medical conditions present in the first radiograph; and comparing the one or more medical conditions present in the first radiograph with one or more treatment codes included in the insurance claim information, wherein the recommendation for the insurance carrier to deny the first insurance claim is based in further part on whether the one or more treatment codes are associated with the one or more medical conditions detected in the first radiograph.

10. The computer-implemented method of claim 7, wherein the first image depicts one or more of: a medical form, a doctor's note, a screenshot or export from practice management software, a prescription, a patient chart, medical test results, or a filled-in medical form.

11. The computer-implemented method of claim 7 further comprising extracting the first image and a plurality of additional images associated with the first insurance claim from a composite image submitted by the healthcare provider as supporting evidence for the first insurance claim.

12. The computer-implemented method of claim 7, wherein comparing the digital signature generated for the first image to previously generated digital signatures of other images comprises determining a Euclidian distance between signatures.

13. The computer-implemented method of claim 12, wherein the digital signature and the previously generated digital signatures are generated in a manner such that a modified image created by changing image data within a base image will have a generated digital signature that is either identical or close in distance to a separately generated digital signature of the base image.

14. The computer-implemented method of claim 13, wherein the image data changes that have no effect or small effects on the generated digital signature of the modified image relative to the separately generated digital signature of the base image include changing a patient name within the base image, cropping the base image, and rotating the base image.

15. The computer-implemented method of claim 7 further comprising:

determining a likelihood that the first insurance claim is associated with potential fraud;

determining that the likelihood that the first insurance claim is associated with potential fraud meets an approval threshold; and based on the likelihood meeting the approval threshold, sending, via an application programming interface (API) to a computing system associated with the insurance carrier, an indication or recommendation that the first insurance claim be approved by the insurance carrier.

16. The computer-implemented method of claim 7 further comprising:

determining a likelihood that the first insurance claim is associated with potential fraud;

determining that the likelihood that the first insurance claim is associated with potential fraud meets a denial threshold; and based on the likelihood meeting the denial threshold, sending, via an application programming interface (API) to a computing system associated with the insurance carrier, an indication or recommendation that the first insurance claim be denied by the insurance carrier.

17. A computer-readable, non-transitory storage medium storing computer executable instructions that, when executed by one or more computer systems, configure the one or more computer systems to perform operations comprising:

obtaining, for a first insurance claim, insurance claim information and at least a first image associated with the first insurance claim, wherein the first image has been submitted to an insurance carrier by a healthcare provider as supporting evidence of a medical service indicated in the insurance claim information as having been performed by the healthcare provider;

generating a digital signature representing the first image, wherein the digital signature is generated based at least in part on image data within the first image, wherein generating the digital signature representing the first image comprises:

implementing a feature extraction process with respect to the image data within the first image to extract a plurality of features of the image data, wherein the feature extraction process comprises at least one of: (i) providing the image data within the first image as input to a convolutional neural network and extracting the plurality of features of the image data from one or more layers of the convolutional neural network, or (ii) applying mathematical transformations to image intensity data within the first image; and applying a hashing function to at least a subset of the plurality of features of the image data to generate the digital signature representing the first image;

comparing the digital signature generated for the first image to previously generated digital signatures of other images that have been submitted in association with insurance claims other than the first insurance claim, wherein the previously generated digital signatures have been generated using the feature extraction process and the hashing function with respect to image data of the other images;

identifying a match between the digital signature generated for the first image submitted for the first insurance claim and one or more of the previously generated digital signatures of other images submitted in association with the insurance claims other than the first insurance claim;

determining, based on the match identified between the digital signature and the one or more of the previously generated digital signatures, that the first image submitted for the first insurance claim is a duplicate of at least one image previously submitted to the insurance carrier for a different insurance claim other than the first insurance claim;

determining a likelihood that the first insurance claim is associated with potential fraud based at least in part on the match between the digital signature and the one or more of the previously generated digital signatures; and based at least in part on the likelihood, generating a recommendation for the insurance carrier indicating whether the first insurance claim should be one of (a) approved by the insurance carrier, (b) denied by the insurance carrier, or (c) further reviewed by the insurance carrier.

18. The computer-readable, non-transitory storage medium of claim 17, wherein the operations further comprise generating a user interface for presentation to the insurance carrier, wherein the user interface includes information identifying each of a plurality of insurance claims, wherein at least a subset of the plurality of insurance claims are presented in the user interface with a visual indicator of potential fraud as determined from digital signature comparisons.

19. The computer-readable, non-transitory storage medium of claim 18, wherein the at least a subset of the plurality of insurance claims are further presented in the user interface with corresponding selectable options for a user to indicate approval or denial of individual insurance claims presented in association with the visual indicator of potential fraud.

* * * * *